US006121223A

United States Patent [19]

[11] Patent Number: 6,121,223

[45] Date of Patent: Sep. 19, 2000

Dixon et al.

[54] DETERGENT COMPOSITION COMPRISING DYE TRANSFER INHIBITING POLYMER AND WATER SOLUBLE SUNSCREEN

[75] Inventors: Sarah Dixon; Timothy David Finch; Jonathan Frank Warr, all of Port Sunlight, United Kingdom

[73] Assignee: Lever Brothers Company, division of Conopco, Inc., New York, N.Y.

[21] Appl. No.: 09/070,676

[22] Filed: Apr. 30, 1998

[30] Foreign Application Priority Data

Apr. 30, 1997 [EP] European Pat. Off. .............. 97302965

[51] Int. Cl.$^7$ ................................ C11D 3/28; C11D 3/37; A61K 7/42

[52] U.S. Cl. .......................... 510/360; 510/115; 510/276; 510/307; 510/324; 510/340; 510/499; 510/500; 424/59

[58] Field of Search .................................... 510/115, 276, 510/307, 324, 340, 360, 499, 500; 424/59

[56] References Cited

U.S. PATENT DOCUMENTS

| | | | |
|---|---|---|---|
| 4,788,054 | 11/1988 | Bernhardt et al. . | |
| 5,466,802 | 11/1995 | Panandiker et al. | 544/193.2 |
| 5,500,154 | 3/1996 | Bacon et al. | 252/551 |
| 5,804,543 | 9/1998 | Wertz et al. | 510/303 |

FOREIGN PATENT DOCUMENTS

| | | |
|---|---|---|
| 0327927 | 8/1989 | European Pat. Off. . |
| 0403062 | 12/1990 | European Pat. Off. . |
| 0587550 | 3/1994 | European Pat. Off. . |
| 0635566 | 1/1995 | European Pat. Off. . |
| 682145 | 11/1995 | European Pat. Off. . |
| 0523956 | 2/1996 | European Pat. Off. . |
| 0728749 | 8/1996 | European Pat. Off. . |
| 728749 | 8/1996 | European Pat. Off. . |
| 95/13354 | 5/1995 | WIPO . |
| 96/03369 | 2/1996 | WIPO . |
| 97/42286 | 11/1997 | WIPO . |
| 97/45518 | 12/1997 | WIPO . |

*Primary Examiner*—Yogendra Gupta
*Assistant Examiner*—Charles Boyer
*Attorney, Agent, or Firm*—Alan A. Bornstein

[57] ABSTRACT

A detergent composition having excellent color care properties when used to launder colored fabnrics. The composition comprises a dye transfer inhibiting polymer comprising one or more monomeric units containing at least one =N—C(=O) with the proviso that the dye transfer inhibiting agent does not comprise an -oxide group and a water soluble sunscreen.

18 Claims, No Drawings

DETERGENT COMPOSITION COMPRISING DYE TRANSFER INHIBITING POLYMER AND WATER SOLUBLE SUNSCREEN

TECHNICAL FIELD

The present invention relates to a detergent composition that enhances the UV barrier provided by fabric, which mitigates dye transfer between fabrics and which can protect fabric from photofading.

BACKGROUND OF THE INVENTION

The colour of fabrics can be altered during the laundering process or during wear or use by photo fading.

During the laundering process there is a tendency for coloured fabrics to release dye into the wash solution. This is a most persistent and troublesome problem as this released dye can then be transferred onto other fabrics or other parts of the same garment. The fading of coloured fabrics by sunlight during wear and during drying is also a major problem for consumers. Sun fading of fabrics is of specific concern to consumers because the contrast between exposed and unexposed areas makes it particularly noticeable. e.g on collars, inside versus outside of garments, and on wrap around garments such as saris.

In addition consumers rely on the use of clothes to protect them from UV light. It is frequently beneficial to enhace the UV protecton given by clothes.

Surfactant containing dye transfer inhibiting compositions are disclosed in EP-A-0 587 550. The dye transfer inhibition agent is a polymer selected from polyamine N-oxide containing polymers.

EP-A-0 327 927 describes a granular detergent additive comprising water-soluble polymeric compounds based on N-vinylpyrolidone and/or N-vinylimidazole and/or N-vinyloxazolidine and cationic compounds.

Detergent compositions comprising a N-vinylimidazole N-vinylpyrolidone copolymer are disclosed in EP-A-0 635 566 and EP-A-0 635 566.

The use of certain sunscreens has already been discussed in the literature. U.S. Pat. No. 4,788,054 teaches the use of N-phenylphthalisomides as ultraviolet radiation absorbers for cotton, wool, polyester and rayon. Fabric care compositions comprising a water dispersible/water soluble copolymers which prevent photofading are disclosed in EP-A-0 523 956.

WO 95/13354 discloses detergent compositions containing the combination of certain dye transfer inhibiting polymers with certain defined hydrophilic optical brighteners which are bis-[(anilino-triazinyl) amino] stilbene sulphonic acid derivatives, (e.g. as disclosed in EP-A-728 749 and GB-A-2 313 375). However, these compositions do not produce good deposition of fluorescer on the fabric to reduce photofading.

EP-A-403 062 discloses an acidic liquid laundry bleaching additive containing a thickener which comprises an solubilized amine-type fluorescent agent and preferably an amide-type polymer.

WO 96/03369 discloses the use of butylated hydroxy toluene for the protection of surfaces from physical and chemical degradation.

There is however a persistent problem that in a detergent composition it is difficult to formulate a composition that mitigates both photofading and dye transfer of fabrics and yet increases the UV barrier of fabrics due to the incompatibility of the active agents used.

The present invention has now found that the transmission of harmful rays, dye transfer inhibition and photofading of fabric can be mitigated by the use of specific detergent compositions.

DEFINITION OF THE INVENTION

Accordingly we have found that the present application relates to a detergent composition comprising:

a) a dye transfer inhibiting polymer comprising one or more monomeric units containing at least one =N—C(=O) with the proviso that the dye transfer inhibiting agent does not comprise an -oxide group; and b) a water soluble sunscreen.

The invention further relates to the use of a detergent composition as described above to reduce the amount of dye transfer between coloured fabrics in the wash, to reduce the photofading of coloured fabrics and to enhance the UV barrier provided by fabric.

DETAILED DESCRIPTION OF THE INVENTION

The compositions of the invention preferably contain detergent-active compounds (surfactants) and generally detergency builders, and may optionally contain bleaching components and other active ingredients to enhance performance and properties. They also contain a dye transfer inhibiting polymer and a water soluble sunscreen.

Water Soluble Sunscreen

The sunscreen used in the invention is any water soluble sunscreen. In the context of the present invention a sunscreen may be a UV absorber, a material that is a UV barrier and/or an antioxidant.

Suitable sunscreens which are UV absorbers are described in N. A. Saath, Cosmetics and Toiletries Vol 102 March 1987 page 21–39 Classifications given as table 2 on page 22,; N. A. Saath, Evolution of modern sunscreen chemicals pages 3–35; Cosmetics and Toiletries Vol 107 March 1992. Sunscreen use in cosmetic formulas, pages 45–47; Ultra violet absorbers by S. B. Miller, G. R. Lappin, and C. E. Tholstrup in 1968–1969 Modem Plastics Encyclopedia, pages 442–447 and; G. R. Lappin, Encyclopedia of polymer science and technology, vol 14, pages 125–148, Ultra violet radiation absorbers.

Suitable antioxidant materials are disclosed in Kirk-Othmer Encyclopaedia of Chemical Technology, fourth edition, volume 3, pages 424–447.

The level of sunscreen is preferably from 0.025 wt % to 5 wt % of the total composition, more preferably from 0.05 wt % to 2.5 wt %, most preferably from 0.075 wt % to 1 wt %.

It is prefered if the sunscreen is a material which absorbs UV in the UVB region of the spectrum. It is further preferred if the sunscreen is capable of reducing the transmisssion of harmful UV rays through fabrics and thus increasing the ultraviolet protection factor of the fabric.

It is especially advantageous if the sunscreens used with composition of the invention have a structure corresponding to formula (I):

(I)

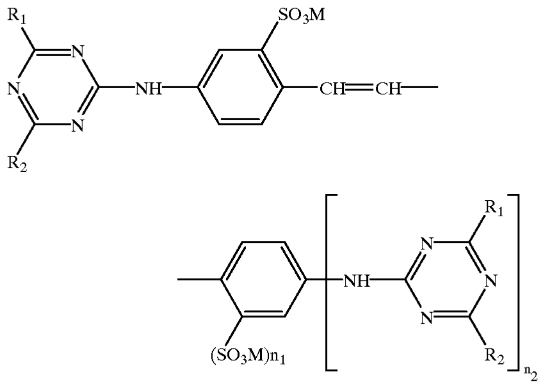

in which M is hydrogen, an alkali metal atom, ammonium or a cation formed from an amine; $R_1$ is a group having one of the formulae:

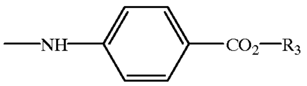

in which $R_3$ is optionally substituted alkyl or optionally substituted aryl;

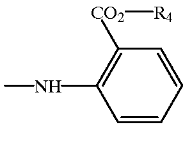

or

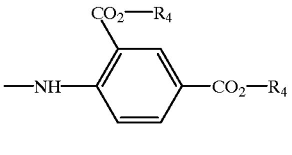

in which $R_4$ is M, optionally substituted alkyl or optionally substituted aryl;

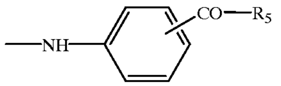

in which $R_5$ is hydrogen, optionally substituted alkyl, optionally substituted aryl or $—NR_7R_8$ in which $R_7$ and $R_8$, independently, are hydrogen, optionally substituted alkyl or optionally substituted aryl, or $R_7$ and $R_8$ together with the nitrogen atom to which they are attached, form a heterocyclic residue;

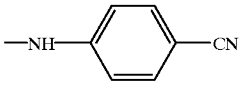

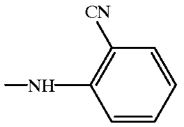

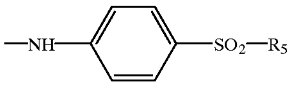

in which $R_8$ is hydrogen, optionally substituted alkyl or optionally substituted aryl, provided that $R_8$ is not carboxymethyl or hydroxymethyl;

$R_2$ is hydrogen, optionally substituted alkyl, optionally substituted aryl,

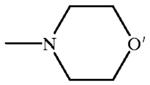

—OH, $—NH_2$, $N(CH_2CH_2OH)_2$, $—N[CH_2CH(OH)CH_3]_2$, $—NH—R_4$, $—N(R_4)_2$ or $—OR_4$, in which $R_4$ has its previous significance; and $n_1$ and $n_2$, independently, are 0 or 1.

Preferred sunscreens of this type and their method of preparation are disclosed in EP 0 728 749 (Ciba Geigy).

It is especially preferred if the sunscreens are of formula (II) and/or formula (III):

(II)

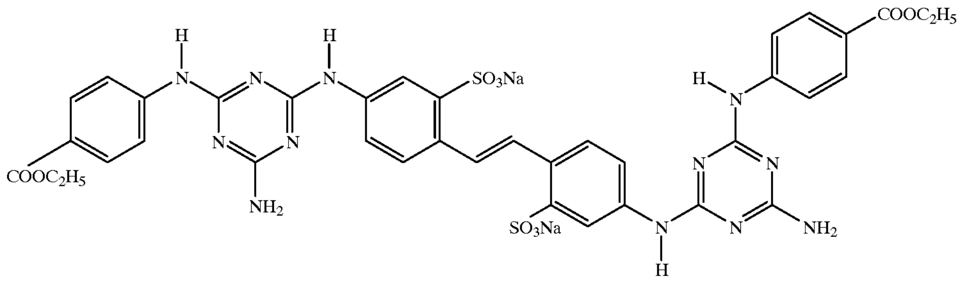

(III)

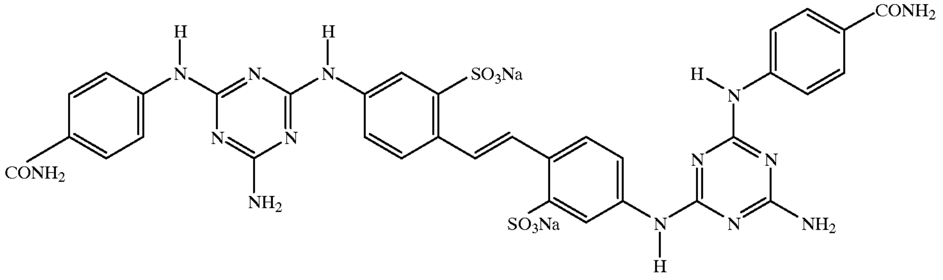

Dye Transfer Inhibition Polymers

The compositions of the invention contain as an essential ingredient a dye transfer inhibiting polymer comprising one or more monomeric units containing at least one =N—C(=O) with the proviso that the dye transfer inhibiting agent does not comprise an -oxide group;

The level of dye transfer inhibition polymer present in the detergent compositions is preferably from 0.01 to 10 wt % of the total composition, more preferably from 0.05 to 5 wt %, most preferably form 0.1 to 1 wt %.

It is preferred if the dye transfer inhibition polymers of the present invention have an average molecular weight range from 500 to 200,000 particularly wherein said polymer has an average molecular weight range 5,000 to 200,000 more preferably from 10,000 to 100,000, most preferably from 20,000 to 70,000.

The dye transfer polymers of the present invention can be used alone or as mixtures of dye transfer polymers.

The nitrogen of the =N—C(=O)— group can be bonded to either one or two other atoms.

Examples of polymers containing =N—C(=O)— groups are:

Polyvinylpyrrolidone:

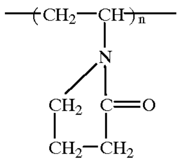

Polyvinyloxazolidone:

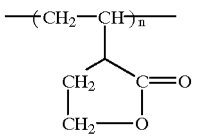

Polyvinylmethyloxazolidone:

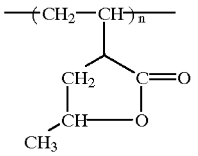

Polyacrylamide and N-substituted polyacrylamides:

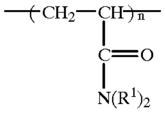

wherein each $R^1$ is independently selected from H and $C_1$–$C_6$ alkyl groups, e.g. methyl, ethyl, propyl, or isopropyl, or two $R^1$ groups can form a 5 or 6 member ring structure.

Polymethacrylamide and N-substituted polymethacrylamides:

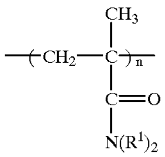

wherein each $R^1$ is as described above.

Poly(N-acrylylglycinamide):

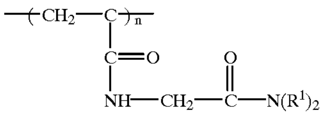

Poly(N-methacrylylglycinamide):

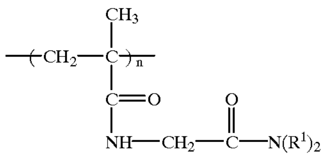

Poly(2-ethyl-2-oxazoline):

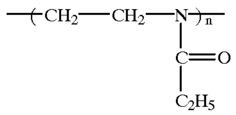

Polyvinylurethane:

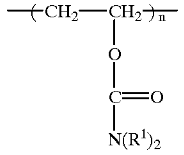

wherein each $R^1$ is as described above. Mixtures of these groups can be present.

These polymers have an amphiphilic character with polar groups conferring hydrophilic properties and apolar groups conferring hydrophobic properties. Preferred polymers are those having the nitrogen atoms highly substituted so that they are shielded to different degrees by the surrounding apolar groups. Examples of said polymers are polyvinylpyrrolidones, polyvinyloxazolidones, N,N-disubstituted polyacrylamides, and N,N-disubstituted polymethacrylamides. Detailed description of physicochemical properties of some of these polymers are given in "Water-Soluble Synthetic Polymers: Properties and Behavior," Vol. I, Philip Molyneux, CRC Press, 1983.

These polymers are also useful in the present invention in partially hydrolyzed and/or crosslinked forms.

A preferred dye transfer inhibitor is polyvinylpyrrolidone (PVP). This polymer has an amphiphilic character with a highly polar amide group conferring hydrophilic and polar-attracting properties, and also has apolar methylene and methine groups, in the backbone and/or the ring, conferring hydrophobic properties. The rings may also provide planar alignment with the aromatic rings, in the dye molecules. PVP is readily soluble in aqueous and organis solvent systems.

PVP is available from ISP, Wayne, N.J., and BASF Corp., Parsippany, N.J., as a powder or aqueous solutions in several viscosity grades, designated as, e.g. K-12, K-15, K-25, and K-30. These K-values indicate the viscosity average molecular weight, as shown below:

| | K-12 | K-15 | K-25 | K-30 |
|---|---|---|---|---|
| PVP Viscosity Avg. Mol. Wt. | 2,500 | 10,000 | 24,000 | 40,000 |

PVP K-12, K-15; and K-30-are-also available from Polyscuebees, Inc. Warrington, Pa., and PVP K-15, K-25, and K30 and poly(2-ethyl-2-oxazoline) are available from Aldrich Chemical Co., Inc. Milwaukee, Wis., Further preferred dye transfer polymers are described in DE 4341072 (BASF), especially preferred are those that contain alkyl-1-vinylimidazole monomers.

The average molecular weight for water-soluble polymers with —N—C(═O)— groups useful in the present invention is from about 500 to about 200,000, preferably from about 500 to about 40,000, and more preferably from about 1,000 to about 30,000.

A further group of preferred polymers for use in detergent compositions according to the present invention comprise a polymer selected from N-vinylimidazole N-vinylpyrrolidone copolymers, Preferably the N-vinylimidazole N-vinylpyrrolidone copolymer of the present invention has a molar ratio of N-vinylimidazole to N-vinylpryrrolidone from 5 to 0.2.

The N-vinylimidazole N-vinylpyrrolidone copolymers can be linear or branched.

It is also advantageous with the present application to use the polymers descrined in GB co-pending application number 97300122.5

Detergent Active Compounds

The detergent compositions of the invention may contain one or more detergent-active compounds (surfactants), preferably in an amount of at least 5% by weight, e.g. from 5% to 30% by weight of total surfactant, based on the total composition may be chosen from soap and non-soap anionic, cationic, nonionic, amphoteric and zwitterionic detergent-active compounds, and mixtures thereof. Many suitable detergent-active compounds are available and are fully described in the literature, for example, in "Surface-Active Agents and Detergents", Volumes I and II, by Schwartz, Perry and Berch.

The preferred detergent-active compounds that can be used are soaps and synthetic non-soap anionic and nonionic compounds.

The detergent compositions of the invention preferably contain an anionic surfactant. A preferred anionic surfactant is alkylbenzene sulphonate, particularly if they are linear alkylbenzene sulphonate, alkylbenzene sulphonates having an alkyl chain length of $C_8$–$C_{15}$ are especially preferred.

It is preferred if the level of anionic surfactant is from 5 wt % to 50 wt %, more preferably 10 wt % to 40 wt %, still more preferably from 12 wt % to 38 wt %, most preferably from 15 wt % to 35 wt %.

Other anionic surfactants suitable for use with the invention are well-known to those skilled in the art. Examples include primary and secondary alkyl sulphates, particularly $C_8$–$C_{15}$ primary alkyl sulphates; alkyl ether sulphates; olefin sulphonates; alkyl xylene sulphonates; dialkyl sulphosuccinates; and fatty acid ester sulphonates. Sodium salts are generally preferred.

The compositions of the invention may also contain nonionic surfactant.

It is preferable if the ratio of anionic surfactant to nonionic surfactant is equal to or greater than 2:3, more preferably greater than or equal to 3:2, most preferably equal to or greater than 4:1.

Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

It is preferred if the level of nonionic surfactant is from 1 wt % to 35 wt %.

The choice of detergent-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

If a high foaming product is desired it is preferable to use nonionic surfactants that are not ethoxylated such as cocomonoethanolamide.

The total amount of surfactant present will also depend on the intended end use and may be as high as 60 wt %, for example, in a composition for washing fabrics by hand. In compositions for machine washing of fabrics, an amount of from 5 to 40 wt % is generally appropriate.

Detergent compositions suitable for use in most automatic fabric washing machines generally contain anionic non-soap surfactant, or nonionic surfactant, or combinations of the two in any ratio, optionally together with soap.

Detergency Builders

The detergent compositions of the invention will generally also contain one or more detergency builders. The total amount of detergency builder in the compositions will suitably range from 5 to 80 wt %, preferably from 10 to 60 wt %.

Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202 (Henkel) and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate are also suitable for use with this invention.

The detergent compositions of the invention preferably contain an alkali metal, preferably sodium, aluminosilicate builder. Sodium aluminosilicates may generally be incorporated in amounts of from 10 to 70% by weight (anhydrous basis), preferably from 25 to 50 wt %.

The alkali metal aluminosilicate may be either crystalline or amorphous or mixtures thereof, having the general formula:

$$0.8\text{–}1.5\ Na_2O.Al_2O_3.0.8\text{–}6\ SiO_2$$

These materials contain some bound water and are required to have a calcium ion exchange capacity of at least 50 mg CaO/g. The preferred sodium aluminosilicates contain 1.5–3.5 $SiO_2$ units (in the formula above). Both the amorphous and the crystalline materials can be prepared readily by reaction between sodium silicate and sodium aluminate, as amply described in the literature.

Suitable crystalline sodium aluminosilicate ion-exchange detergency builders are described, for example, in GB 1 429 143 (Procter & Gamble). The preferred sodium aluminosilicates of this type are the well-known commercially available zeolites A and X, and mixtures thereof.

The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP 384 070A (Unilever). Zeolite MAP is defined as an alkali metal aluminosilicate of the zeolite P type having a silicon to aluminium ratio not exceeding 1.33, preferably within the range of from 0.90 to 1.33, and more preferably within the range of from 0.90 to 1.20.

Especially preferred is zeolite MAP having a silicon to aluminium ratio not exceeding 1.07, more preferably about 1.00. The calcium binding capacity of zeolite MAP is generally at least 150 ma CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di- and, trisuccinates, carboxymethyloxysuccinates, carboxymethyloxymalonates, dipicolinates, hydroxyethyliminodiacetates, alkyl- and alkenylmalonates and succinates; and sulphonated fatty acid salts. This list is not intended to be exhaustive.

Especially preferred organic builders are citrates, suitably used in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Bleach Components

Detergent compositions according to the invention may also suitably contain a bleach system. Fabric washing compositions may desirably contain peroxy bleach compounds, for example, inorganic persalts or organic peroxyacids, capable of yielding hydrogen peroxide in aqueous solution. Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in an amount of from 0.1 to 35 wt %, preferably from 0.5 to 25 wt %.

The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors caprolactam precursors and pernonanoic acid precursors. Especially preferred bleach precursor suitable for use in the present invention are N,N,N',N'-tetracetyl ethylenediamine (TAED) and sodium nonanoyloxybenzene sulphonate (SNOBS). The novel quaternary ammonium and phosphonium bleach precursors disclosed in U.S. Pat. No. 4,751,015 and U.S. Pat. No. 4,818,426 (Lever Brothers Company) and EP 402 971A (Unilever) are also of great interest. The cationic bleach precursors disclosed in EP 284 292A and EP 303 520A (Kao) may also be used.

The bleach system can be either supplemented with or replaced by a peroxyacid. Examples of such peracids can be found in U.S. Pat. No. 4,686,063 and U.S. Pat. No. 5,397,501 (patent on TPCAP-Unilever). A preferred example is the imido peroxycarboxylic class of peracids described in EP A 325 288, EP A 349 940, DE 382 3172 and EP 325 289. A particularly preferred example is phtalimido peroxy caproic acid (PAP). Such peracids are suitably present at 0.1–12%, preferably 0.5–10%.

A bleach stabiliser (heavy metal sequestrant) may also be present. Suitable bleach stabilisers include ethylenediamine tetraacetate (EDTA), the polyphosphonates such as Dequest (Trade Mark) and non-phosphate stabilisers such as EDDS (ethylene diamine di-succinic acid). These Bleach stabilisers are also useful for stain removal, especially in products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

The Enzyme

Suitable enzymes include the proteases, amylases, cellulases, oxidases, peroxidases and lipases usable for incorporation in detergent compositions.

Preferred proteolytic enzymes (proteases) are, catalytically active protein materials which degrade or alter protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4–12 are available and can be used in the instant invention. Examples of suitable proteolytic enzymes are the subtilisins, which are obtained from particular strains of *B. subtilis* and *B. licheniformis,* such as the commercially available subtilisins Maxatase (Trade Mark), as supplied by Gist-Brocades N. V., Delft, Holland, and Alcalase (Trade Mark), as supplied by Novo Industri A/S, Copenhagen, Denmark.

Particularly suitable is a protease obtained from a strain of Bacillus having maximum activity throughout the pH range of 8–12, being commercially available, e.g. from Novo Industri A/S under the registered trade-names Esperase (Trade Mark) and Savinase (Trade-Mark). The preparation of these and analogous enzymes is described in GB 1 243 785. Other commercial proteases are Kazusase (Trade Mark) (obtainable from Showa-Denko of Japan), Optimase (Trade Mark) (from Miles Kali-Chemie, Hannover, West Germany), and Superase (Trade Mark) (obtainable from Pfizer of U.S.A.).

Detergency enzymes are commonly employed in granular form in amounts of from about 0.1 to about 3.0 wt %.

Other Ingredients

The compositions of the invention may contain alkali metal, preferably sodium, carbonate, in order to increase detergency and ease processing. Sodium carbonate may suitably be present in amounts ranging from 1 to 60 wt %, preferably from 2 to 40 wt %. However, compositions containing little or no sodium carbonate are also within the scope of the invention.

Powder flow may be improved by the incorporation of a small amount of a powder structurant, for example, a fatty acid (or fatty acid soap), a sugar, an acrylate or acrylate/maleate polymer, or sodium silicate.

One preferred powder structurant is fatty acid soap, suitably present in an amount of from 1 to 5 wt %.

Other materials that may be present in detergent compositions of the invention include sodium silicate; antiredeposition agents such as cellulosic polymers; inorganic salts such as sodium sulphate; lather control agents or lather boosters as appropriate; proteolytic and lipolytic enzymes; dyes; coloured speckles; perfumes; foam controllers; fabric softening compounds, soil release polymers, fluorescers and decoupling polymers. This list is not intended to be exhaustive.

The detergent composition when diluted in the wash liquor (during a typical wash cycle) will give a pH of the wash liquor from 7 to 10.5.

The detergent components of the present invention may be incorporated in detergent compositions of all physical types, for example, powders, liquids, gels and solid bars.

Detergent compositions of the invention may be prepared by any suitable method.

Particulate detergent compositions are suitably prepared by spray-drying a slurry of compatible heat-insensitive ingredients, and then spraying on or postdosing those ingredients unsuitable for processing via the slurry. The skilled detergent formulator will have no difficulty in deciding which ingredients should be included in the slurry and which should not.

Particulate detergent compositions of the invention preferably have a bulk density of at least 400 g/l, more preferably at least 500 g/l.

Especially preferred compositions have bulk densities of at least 650 g/liter, more preferably at least 700 g/liter.

Such powders may be prepared either by post-tower densification of spray-dried powder, or by wholly non-tower methods such as dry mixing and granulation; in both cases a high-speed mixer/granulator may advantageously be used.

Processes using high-speed mixer/granulators are disclosed, for example, in EP-A-340 013, EP-A-367 339, EP-A-390 251 and EP-A-420 317.

Liquid detergent compositions can be prepared by admixing the essential and optional ingredients thereof in any desired order to provide compositions containing components in the requisite concentrations. Liquid compositions according to the present invention can also be in compact form which means it will contain a lower level of water compared to a conventional liquid detergent.

EXAMPLES

The invention will now be illustrated by the following non-limiting examples. In the examples all percentages are expressed by weight.

Comparative Examples are designated by letters, while Examples of the invention are designated by numbers.

To demonstrate the improved desposition of sunscreen in the presence of specific dye transfer polymers of the following Examples were prepared,

| Components | Examples Wt. (g) A | B | C | 1 | 2 | 3 | 4 | 5 | 6 |
|---|---|---|---|---|---|---|---|---|---|
| Nonionic/Anionic Surfactant Mixture(1) | 0.25 | 0.40 | 0.45 | 0.25 | 0.40 | 0.45 | 0.25 | 0.40 | 0.45 |
| Nonionic/Anionic Surfactant Mixture(2) | 0.25 | 0.10 | 0.05 | 0.25 | 0.10 | 0.15 | 0.25 | 0.10 | 0.05 |
| Sunscreen(3) | 0.0044 | 0.0044 | 0.0044 | 0.0044 | 0.0044 | 0.0044 | 0.0044 | 0.0044 | 0.0044 |
| PVP(4) | — | — | — | 0.0109 | 0.0109 | 0.0109 | — | — | — |
| PVP/PVI(5) | — | — | — | — | — | — | 0.0109 | 0.0109 | 0.0109 |
| PVPy-N-Oxide(6) | 0.0109 | 0.0109 | 0.0109 | — | — | — | — | — | — |
| Sodium tripolyphosphate | 0.44 | 0.44 | 0.44 | 0.44 | 0.44 | 0.44 | 0.44 | 0.44 | 0.44 |
| Sodium bicarbonate | 0.261 | 0.261 | 0.261 | 0.261 | 0.261 | 0.261 | 0.261 | 0.261 | 0.261 |
| Water | balance to 500 g | | | | | | | | |

(1)is LAS - Petrelab 550 (ex Petresa)
(2)is ($C_{12-15}$) 7EO Synperonic A7 (ex Shell)
(3)is the compound of formula II
(4)is Sokalan HP50 (trademark ex BASF)
(5)is ZK535/95 (trademark ex BASF)
(6)ex Polysciences Inc.

The components of table 1 were mixed together for 10 minutes. 12.5 g of white cotton were added to the mixture and washed at 40° C. in demineralised water in a tergometer at 100 rpm. The cloths were then rinsed in demineralised water, spun and line dried.

As in this case the sunscreen was a fluorescent material, fluorescent measurements were used to monitor its delivery to the fabric.

The fluorescer intensity of the washed cloths were measured on a Perkin Elmer Luminescence spectrometer LS 50 at 442 nm.
A high result indicates that there is a high level of sunscreen deposited on the fabric.

| Example | Fluorescence Intensity |
|---|---|
| A | 94.4 |
| B | 113.6 |
| C | 131.9 |
| 1 | 127.1 |
| 2 | 138.2 |
| 3 | 139.8 |
| 4 | 98.8 |
| 5 | 121.1 |
| 6 | 134.5 |

It can this be seen that Examples with PVP and PVP/PVI deposit the sunscreen better than Examples with PVP-N-oxide.

The following compositions were prepared according to the invention:

Example 7

| | |
|---|---|
| Na PAS | 11.5 |
| NI 7EO | 6.3 |
| Soap | 2.0 |
| Zeolite A24 | 24.1 |
| SCMC | 0.6 |
| Na Citrate | 10.6 |
| Carbonate | 23.0 |
| Soil release polymer | 0.8 |
| EAG | 3.7 |
| PVP | 0.1 to 1 |
| Sunscreen of formula II | 0.1 to 1 |

-continued

| | |
|---|---|
| Fluorescer | — |
| EDTMP | 0.4 |
| Percarbonate | — |
| CP5 type polymer | 0.9 |
| Protease | 0.7 |
| Lipase | 0.1 |
| Perfume | 0.4 |
| Water/salts | to 100 |

Example 8

| | |
|---|---|
| Na LAS | 7.1 |
| NI 7EO | 4.7 |
| NI 3EO | 3.5 |
| Soap | 0.3 |
| Fatty Acid | 0.3 |
| STPP | 27.1 |
| SCMC | 0.2 |
| Na silicate | 7.1 |
| CP5 polumer | 1.2 |
| Sulphate | 16.5 |
| Soil release polymer | 0.4 |
| Sunscreen of formula II | — |
| PVP | 0.1–1 |
| EAG | 1.28 |
| Carbonate | 12.00 |
| Bicarbonate | 6.00 |
| Protease | 0.18 |
| Cellulase | 0.20 |
| Lipase/Amylase | 0 to 2% |
| Clay | 0 to 10% |
| Cationic surfactant | 0 to 0.2 |
| Salts/water | to 100 |

Examples 9 and 10

| Ingredient | Wt % Example 9 | Example 10 |
|---|---|---|
| Alkyl Sulphate | — | 10 |
| Linear Alkyl Benzene Sulphonate | 10 | — |

-continued

| | Wt % | |
|---|---|---|
| Ingredient | Example 9 | Example 10 |
| Alkyl ethoxy sulphate | 7 | 7 |
| Fatty alcohol ethoxylate 7EO | 6 | 6 |
| Sodium Citrate $2H_2O$ | 5 | 5 |
| Propylene glycol | 8 | 8 |
| Sorbitol | 4.5 | 4.5 |
| Na tetra-borate $5H_2O$ | 3 | 3 |
| Enzyme | to 2% | to 2% |
| Soil release polymer | to 2% | to 2% |
| Sunscreen of formula II | 0.1 to 1 | 0.1 to 1 |
| PVP/PVI | 0.1 to 1 | 0.1 to 1 |
| Water/minors | to 100 | to 100 |

What is claimed is:

1. A detergent composition comprising:

a) a dye transfer inhibiting polymer formed solely of non-oxide monomer units which monomer units comprise at least one =N—C(=O); and b) a water soluble sunscreen, in which the sunscreen has the formula (I)

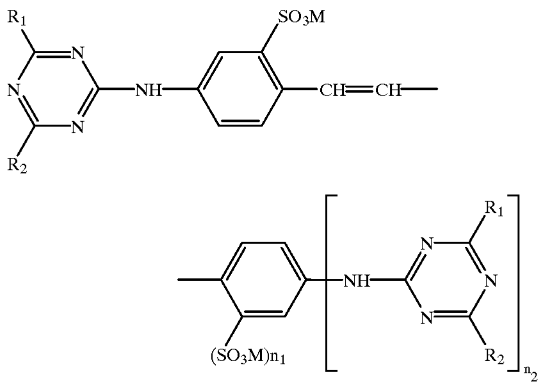

in which M is hydrogen, an alkali metal atom, ammonium or a cation formed from an amine; $R_1$ is a group having one of the formulae:

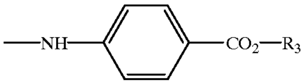

in which $R_3$ is optionally substituted alkyl or optionally substituted aryl;

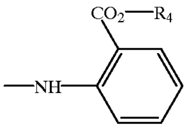

or

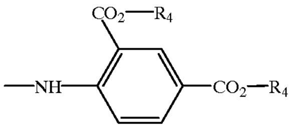

in which $R_4$ is M, optionally substituted alkyl or optionally substituted aryl;

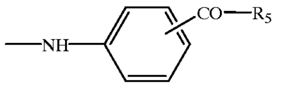

in which $R_5$ is hydrogen, optionally substituted alkyl, optionally substituted aryl or —$NR_7R_8$ in which $R_7$ and $R_8$, independently, are hydrogen, optionally substituted alkyl or optionally substituted aryl, or $R_7$ and $R_8$, together with the nitrogen atom to which they are attached, form a heterocyclic residue;

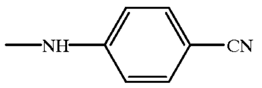

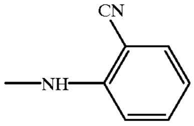

or

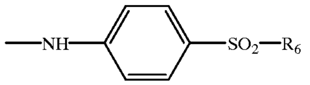

in which $R_6$ is hydrogen, optionally substituted alkyl or optionally substituted aryl, provided that $R_6$ is not carboxymethyl or hydroxymethyl;

$R_2$ is hydrogen, optionally substituted alkyl, optionally substituted aryl,

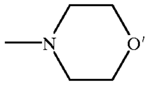

—OH

—$NH_2$, —$N(CH_2CH_2OH)_2$, —$N[CH_2CH(OH)CH_3]_2$, —NH—$R_4$, $N(R_4)_2$ or —$OR_4$, in which $R_4$ has its previous significance; and $n_1$ and $n_2$, independently, are 0 or 1.

2. The detergent composition of claim 1, further comprising at least 5% by weight of surfactant material.

3. The detergent composition of claim 1, further comprising from 5% to 50% of the total composition of anionic surfactant.

4. The composition of claim 3, comprising from 10% to 40% by weight of the total composition of anionic surfactant.

5. The composition of claim 3, comprising from 12% to 38% by weight of the total composition of anionic surfactant.

6. The composition of claim 3, comprising from 15% to 35% by weight of the total composition of anionic surfactant.

7. The detergent composition of claim 1, further comprising from 1% to 35% by weight of the total composition of nonionic surfactant.

8. The detergent composition of claim 1, further comprising nonionic and anionic surfactant in which the ratio of anionic surfactant to nonionic surfactant is equal to or greater than 2:3.

9. The detergent composition of claim 1, in which the sunscreen has the formula (II):

(II)

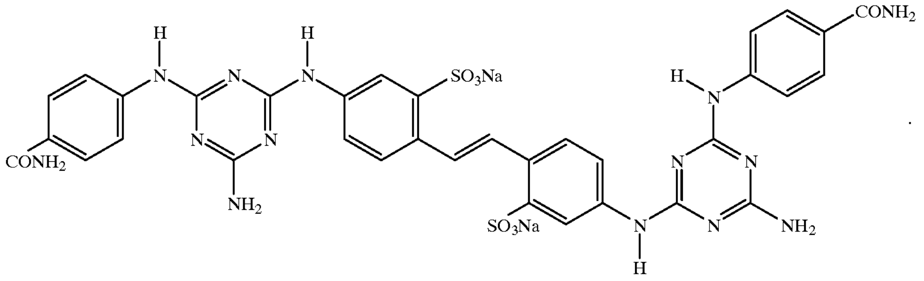

10. The detergent composition of claim 1, in which the sunscreen has the formula (III):

(III)

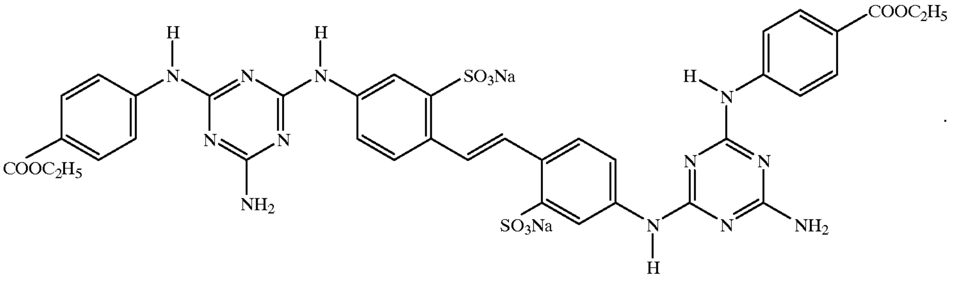

11. The detergent composition of claim 1, in which the level of sunscreen (b) is from 0.025 wt % to 5 wt % of the total composition.

12. The detergent composition of claim 1, in which the dye transfer inhibiting agent (a) comprises polyvinyl pyrrolidone or a co-polymer thereof.

13. The detergent composition according to claim 1, in which the dye transfer inhibiting agent has a molecular weight from 500 to 200,000.

14. The detergent composition of claim 1, in which the level of dye transfer inhibiting agent is from 0.01 wt % to 10 wt % of the total composition.

15. A method of reducing dye transfer between colored fabrics during washing, the method comprising:

(a) dissolving in water, a composition according to claim 1 to form a wash liquor; and (b) washing said fabrics in the wash liquor.

16. A method of reducing photofading of a colored fabric during washing, the method comprising:

(a) dissolving in water, a composition according to claim 1 to form a wash liquor, and (b) washing said fabric in the wash liquor.

17. A method of enhancing UV barrier property of a fabric, the method comprising: (a) dissolving in water, a composition according to claim 1 to form a wash liquor, and (b) washing said fabric in the wash liquor.

18. The detergent composition of claim 1, in which the water soluble sunscreen is a material which absorbs UV in the UV-B region of the spectrum.

* * * * *